(12) United States Patent
Brabec (10) Patent No.: US 10,296,713 B2
(45) Date of Patent: May 21, 2019

(54) METHOD AND SYSTEM FOR REVIEWING MEDICAL STUDY DATA

(71) Applicant: TomTec Imaging Systems GmbH, Unterschleissheim (DE)

(72) Inventor: Stefan Brabec, Poing (DE)

(73) Assignee: TOMTEC IMAGING SYSTEMS GMBH, Unterschleissheim (DE)

(*) Notice: Subject to any disclaimer, the term of this patent is extended or adjusted under 35 U.S.C. 154(b) by 38 days.

(21) Appl. No.: 14/982,329

(22) Filed: Dec. 29, 2015

(65) Prior Publication Data

US 2017/0186129 A1 Jun. 29, 2017

(51) Int. Cl.
*G06F 19/00* (2018.01)

(52) U.S. Cl.
CPC ............ *G06F 19/321* (2013.01); *G06F 19/00* (2013.01); *G06F 19/324* (2013.01)

(58) Field of Classification Search
CPC ........... G06T 1/20; G06T 1/0007; G06T 1/60; G06T 2200/16; G06T 2200/24; G06T 2210/36; G06T 2210/41; G06F 19/321; G06F 19/324; G09G 5/005; G09G 2354/00; G09G 2380/08
See application file for complete search history.

(56) References Cited

U.S. PATENT DOCUMENTS

| | | | |
|---|---|---|---|
| 6,934,698 B2 | 8/2005 | Judd et al. | |
| 7,457,656 B2 | 11/2008 | Judd et al. | |
| 8,166,381 B2 | 4/2012 | Judd et al. | |
| 8,712,120 B1* | 4/2014 | Reicher | H04L 67/02 382/128 |
| 2009/0100125 A1* | 4/2009 | McDowell | G06F 17/30902 709/203 |
| 2010/0141650 A1* | 6/2010 | Abdo | G06T 9/001 345/420 |
| 2011/0145878 A1* | 6/2011 | Gronning | H04N 21/234363 725/116 |
| 2011/0249861 A1* | 10/2011 | Tokutake | G06F 17/3079 382/103 |
| 2012/0117145 A1 | 5/2012 | Clift et al. | |

(Continued)

OTHER PUBLICATIONS

"DICOM Web Viewer"; Retrieved on Jan. 14, 2016; pp. 1-3; Retrieved from http://ivmartel.github.io/dwv/.

(Continued)

*Primary Examiner* — Jacinta M Crawford
*Assistant Examiner* — Phuc N Doan (57) ABSTRACT

There is described a method and a system including a viewing application running on a user's device configured to create a user interface including a drawable region on the user's device, a server environment including a coordinator engine to receive requests for review sessions from the viewing application, and a review helper process, allocated to each review session by the coordinator engine. The helper process retrieves medical study data from a data storage and transfers a stream of drawing commands to the viewing application. At least part of the drawing commands are cached on the user's device, so that the helper will not transfer the cached drawing commands again, and/or will transfer a drawing command relating only to a difference between one frame and the next.

18 Claims, 5 Drawing Sheets

(56) References Cited

U.S. PATENT DOCUMENTS

| | | | | |
|---|---|---|---|---|
| 2013/0054679 | A1* | 2/2013 | Jooste | G06F 9/54 709/203 |
| 2014/0074913 | A1* | 3/2014 | Claydon | H04L 67/42 709/203 |
| 2014/0111528 | A1* | 4/2014 | Lifshitz | G06T 1/20 345/522 |
| 2014/0133632 | A1* | 5/2014 | Wakai | A61B 5/00 378/98 |
| 2014/0143298 | A1 | 5/2014 | Klotzer et al. | |
| 2014/0154648 | A1* | 6/2014 | Gonsalves | G06Q 10/10 434/219 |
| 2015/0089365 | A1* | 3/2015 | Zhao | G06F 19/321 715/708 |
| 2016/0092446 | A1* | 3/2016 | Nye | G06F 17/3028 705/3 |
| 2016/0232369 | A1* | 8/2016 | Nuggehalli | G06F 21/6218 |

OTHER PUBLICATIONS

"HTML5 DICOM Viewer: First Try"; Retrieved on Jan. 14, 2016; pp. 1-4; Retrieved from http://fernandojsg.com/blog/html5-dicom-viewer-first-try/.

DCM4CHE Support Forums; "Proof of Concept—View 16 Bit DICOM Images in the Browser without a Plugin"; Retrieved on Jan. 14, 2016; pp. 1-2; Retrieved from http://forums.dcm4che.org/jiveforums/thread.jspa?threadID=2509.

DCM4CHE Support Forums; "WebGL 3D Viewer Demo"; Retrieved on Jan. 14, 2016; pp. 1-4; Retrieved from http://forums.dcm4che.org/jiveforums/thread.jspa?threadID=4233.

GitHub: Benchmark; Retrieved on Jan. 14, 2016; pp. 1-4; Retrieved from https://github.com/ivmartel/dwv/wiki/Benchmark.

GitHub; Retrieved on Jan. 14, 2016; pp. 1-4; Retrieved from https://github.com/xtk/X#readme.

Wessels et al.; "Remote Data Visualization through WebSockets"; 2011 Eighth International Conference on Information Technology: New Generations; Jan. 2011; pp. 1-3; Retrieved from www.researchgate.net/publication/220841458_Remote_Data_Visual.

European Search Report for EP Application No. 15202551; Date of Search Apr. 21, 2016; 14 pages.

Jailly; "Toward Collaborative and Contextualized Online Instrumentation in Pervasive and Ubiquitous Environments"; Telecom, Version 1; 2014; pp. 1-210.

Joveski; "Dispositif de rendu distant multimedia et semantique pour terminaux legers collaboratifs"; Paris Tech; 2012; pp. 1-140.

Tsymbal et al.; "Towards Cloud-Based Image-Integrated Similarity Search in Big Data"; IEEE; 2014; pp. 593-596.

Simoens et al "Optimized mobile thin clients through a MPEG-4 BiFS semantic remote display framework"; ResearchGate; Multimedia Tools and Applications; Nov. 2012; https://www.researchgate.net/publication/227062897.

* cited by examiner

Client Side

Server Side

Frame 100: TS = 30ms

Frame 101: TS = 55ms

Frame 102: TS = 80ms

.....

Frame 106: TS = 180ms

Frame 107: TS = 30ms

Fig. 5

Vertex Buffer 1

| 0 | x | y | z | R | G | B | A |
|---|---|---|---|---|---|---|---|
| 1 | | | | | | | |
| 2 | | | | | | | |
| 3 | | | | | | | |
| 4 | | | | | | | |
| 5 | | | | | | | |
| 6 | | | | | | | |

Vertex Buffer 2

| 0 | |
|---|---|
| 1 | |
| 2 | |
| 3 | |
| 4 | |

Texture 1

Texture 2 
32 mm

Texture 3

Fig. 6

METHOD AND SYSTEM FOR REVIEWING MEDICAL STUDY DATA

TECHNICAL FIELD

The present invention relates to a method and system for reviewing medical study data by means of a viewing application running on a user's device.

BACKGROUND

In modern medical diagnosis, a number of medical imaging modalities as well as other means of acquiring measurements data from patents for the purposes of diagnosis are known, for example medical ultrasound, CT (computed tomography), MRI (magnetic resonance imaging), X-ray imaging, SPECT (single photon emission photography) and PET (positron emission tomography) and ECG (electrocardiogram), to name just some examples. Therefore, a substantial amount of data is generated, often by several modalities, for one patient which may be stored within a picture archiving and communication system (PACS), or any other database. The data produced by such imaging or other diagnostic modality is called "medical study data" in this application, wherein often the data acquired from one patient in one diagnosis session is stored in one study.

Often, studies are analysed not directly after acquisition but at a later time by a specialized physician or other medical personnel. In order to review and analyze the medical study data, it is sometime required to perform computationally intensive measurements and calculations, such as segmenting images to find different compartments, fitting models to organs in the body, or, in the case of cardiac imaging calculating important parameters such as cardiac output, reflow at heart valves etc. For performing such analyses, it has been hitherto been the practice to install dedicated software on the users' devices, e.g. on their workstations, PCs or laptops. An example of such software for analysing medical ultrasound images is the product Image Arena™ by the applicant, which is a multi modality platform for image analysis, review and data management, providing a comprehensive portfolio of clinical and advanced applications for 2D (two-dimensional), 3D (three-dimensional) and 4D (four-dimensional) analysis.

Accordingly, it is necessary for medical practitioners to download and regularly update the data analysis software, and the provider of such software is required to provide different versions of the software for all prevalent operating systems, to test the software for all operating systems and to alert the users of required updates.

The patents by Heart Imaging Technologies, LLC, in particular U.S. Pat. Nos. 7,457,656, 8,166,381, and 6,934,698 provide a medical image management system to allow any conventional internet browser to function as a medical workstation. The system may be used to convert medical images from a plurality of image formats to browser-compatible format. However, this solution requires high bandwidth and a low-latency network, since the complete images in the browser-compatible format are transferred from server to client. A further system to display and facilitate image manipulation of image content via a browser disclosed in US 2014/0143298 A1, wherein a data manager formats image content to a browser-convenient format.

SUMMARY

Accordingly, it is the object of the invention to overcome the disadvantages of the prior art by creating a method and system in which the user has a desktop application user experience, but does not require a high bandwidth internet connection or network in order to process and analyse large data files such as three dimensional (3D) or four dimensional (4D) images (wherein the fourth dimension is time). It is another object of the invention to provide a software solution for reviewing medical data in which no client installations such as upgrades, downgrades, configuration and deployment are necessary. It is another object of the invention to provide a software solution for reviewing medical data in which the software, once written, can run anywhere without plugins, and can be accessed everywhere by users. It is a further object of the invention to provide a method for reviewing medical image data which provides diagnostic image quality, both spatial and temporal, even if the images are downloaded from a remote server at a low bandwidth, high-latency network.

The objects of the invention are met by methods according to claims 1 and 6, the system according to claim 14 and the computer program product according to claim 13.

The invention provides a distributed architecture for medical image viewing, with a part that runs in a server environment, which is usually a controlled, secure environment, for example a process on a server machine, a thread in a process running of the server machine, a container (light-weight virtual machine), a virtual machine, cloud instance, etc., and another part that runs on the users' personal device, e.g. inside an internet browser running on a PC, tablet or smartphone (i.e. a web application), or as a desktop application running on the computer's operating system (e.g. Windows, Linux) or using any other runtime environment or interpreter (e.g. Java, Ruby, Python), or as an application for mobile devices ("mobile application" or "app"), which is distributed via channels like Apple's AppStore, GooglePlay or via intranet. However, for the user the two parts function like a virtual single application.

The part running on the user's personal device is called "viewing application", whereas the part that runs in a server environment includes a "helper process" or "helper", and in some embodiments a "coordinator engine". In contrast to prior art applications, the helper does not render and transfer entire images to be displayed on the user's device but rather encodes and transfers drawing commands to be processed by the client, i.e. the viewing application. Further, helper and viewing application know each other's state, for example because they have a 1:1 connection. Accordingly, computations can be distributed between helper and viewing application in an optimized manner, which is not possible in a stateless, multi-client rendering architecture or with a remote-desktop protocol. Accordingly, in useful embodiments, the helper is a stateful component, and the viewing application is able to cache complete drawing commands, or parts thereof, such as related data buffers, or sequences of drawing commands. Since the helper knows what has been sent to the viewing application and has been cached by it, it is able to adapt the further stream of drawing commands such that cached data is not resent. This leads to lower requirements regarding bandwidth of the communication channel, i.e. the network connection between helper and viewing application.

It is an advantage of the present invention that medical study data which are too large to be processed by the user's device (memory CPU, network bandwidth), do not have to be fully transferred to the user's device but may be handled by the helper process in a secure and computationally fast server environment. At the same time, it is possible to make the viewing application as general and thin as possible, for example, it might even be a web application running inside the user's web browser. This will reduce the workload for testing a complete and complex application for all combinations of browsers, browser versions and/or operating systems, which is otherwise necessary in a heterogeneous client environment.

On the other hand, program parts that are not available on the user's device, for example, not available for the browser environment, can be performed by the helper. The same is true where e.g. the browser lacks certain capabilities needed to perform calculations. Further, the helper process may be configured not to transfer sensitive/confidential data (e.g. patient data or confidential program code) to the user's device, which may be in an untrusted environment (e.g. when the user's device gets stolen or high-jacked by malicious software).

The medical study data to be reviewed on the user's device may contain medical image data, e.g. ultrasound, CT, MRI data or image data generated by other modalities, as well as further measurement data such as ECG data etc., in addition to patient parameters such a name, age etc. In useful embodiments, the medical study data is present in the format in which it is supplied by the modality manufacturer, in DICOM standard or any other state of the art format. The medical study data may be stored in the same server environment where the helpers are running, but it may also be stored on a different server accessible by a network connection, or possibly even on the user's device. The invention is functioning independent of the source of the medical study data.

In useful embodiments, the user will first be able to access a list of medical studies and select one (possibly stored on a hospital or other database server).

Accordingly, the viewing application will pass on information on the selected medical study e.g. to the coordinator engine before or after or together with the request for a review session, or alternatively directly to the helper process once the communication channel has been set up. In any case, the helper process is able to communicate with the server where the medical study data is stored and to retrieve the required data.

In useful embodiments, the viewing application, or at least updates to the viewing application, are loaded onto the user's device, preferably from a web server, preferably without user intervention, and whenever required, e.g. prior to each review session. In useful embodiments, the viewing application is completely loaded onto the user's device before each review session, e.g. if the viewing application is a web application, it is loaded into the user's web browser. Thus, the viewing application does not have to be regularly updated by the user. In useful embodiments, the viewing application is—or at least can be—deleted from the user's device without any trace after each session. In useful embodiments, the user can initiate a session from all of his client devices (mobile phone, tablet computer, home PC, work PC) without having to install software, or at the most a small app.

The viewing application can be one or more programs, which act as the client. In useful embodiments, they can be run by the browser's run time environment (e.g. Java script program, web assembly). The loading process of this program can be independent from the other system components (coordinator engine, helper) described here, e.g. served by a dedicated web server or CDN (Content Delivery Network). An example would be a single page application, not a server-based application. However, the invention also covers examples where the viewing application is installed on the user's device (desktop application). In all cases, the functionality required for analysing medical data is distributed between client (viewing application) and server environment (helper).

The viewing application includes program code to create a user interface which includes a drawable region on the user's device. The drawable region is the diagnostic area where images and other study data are to be displayed. It is for example a rendering element (e.g. HTML5 Canvas) that can be used for fast, even graphics-card assisted 2D and 3D drawings. The user interface may further comprise user interface/input elements such as buttons, sliders, dialogs as well as the general layout which, in the case of a web application, are created by the viewing application directly in the browser.

When the viewing application sends a request for a review session to a (usually remote) first server, it is in useful embodiments first handled by a so-called coordinator engine. This coordinator engine is responsible for allocating at least one helper process in the server environment. The helper process may be created new for each review session, or may be chosen from a pool of prepared helpers (warm stand-by). In useful embodiments, the coordinator engine will pass the connection information of the helper process (e.g. URL, token, . . . ) to the viewing application, which is then able to prepare one or multiple direct connection(s) or communication channel(s) from viewing application to helper. Alternatively, a proxy can be used to dispatch network connections from a dedicated server to the helpers.

The coordinator engine is responsible e.g. for lifecycle (starting, creating, allocating and closing helpers), load balancing in the server environment where the helpers are running, fail-over and initial authentication of the user. The latter can be done by creating a one-time token passed from the viewing application to the server environment (coordinator engine and/or helper process) via a secure connection. In useful embodiments, the communication channel is secure.

In useful embodiments, each viewing application then establishes a direct connection to a helper process. Alternatively, a proxy can be used to dispatch network connections from a dedicated server to the helper(s). In useful examples, HTML5 web sockets are used for low-latency, high-bandwidth connections. For performance reasons, the viewing application may also open multiple connections to its helper. Securing the communication is the responsibility of the communication channel, e.g. using a secure network protocol, like SSL web sockets. For further performance improvements, stream or message based compression may be used (like gzip). These connections are all examples for the at least one "communication channel" referred to in the following.

The way the helper process and the viewing application communicate in preferred embodiments is described in the following: In order to analyse medical study data, it is usually necessary to display images as well as overlays, such as measurements, text annotations, graphical displays, etc. Nearly every software for medical image analysis therefore has some kind of drawing layer in its software architecture that can be used to define drawing primitives like lines, polygons, textured polygons, text in both 2D and 3D. Often, the items to be displayed are organized in a hierarchical "scene graph". Rendering (drawing) a hierarchical scene graph is done by traversing the scene graph nodes and generating more low-level drawing calls for an underlying graphics API (application programming interface), like DirectX or OpenGL.

In useful embodiments of the invention, the helper process is in charge of maintaining the complete scene graph. For example, the helper process might use a selected medical study data to perform some measurements or analysis thereon (usually at the request of the user communicated via the above-mentioned user interface on the viewing application), and will create a graphical overlay, e.g. a text annotation or a chart which contains the results of the analysis.

However, the helper process will not render (draw) the chart or text annotation itself. It will e.g. only create a scene graph containing these items. The scene graph may also include a texture including image data from the medical study data.

The helper process will (e.g. from such scene graph), generate a stream of drawing commands which it then transfers to the viewing application through the communication channel. For example, the helper process will encode the drawing commands relating to a scene graph into a command stream which is then transferred to the client/viewing application. The "stream of drawing commands" e.g. contains instructions on how to render the image to be displayed in the drawable region. In useful embodiments, individual items in the image (e.g. a medical image or part thereof, and overlays such as a text annotation, a chart or other graphical display) are encoded in individual drawing commands, and/or the data related thereto is encoded in associated data buffers (e.g. textures and vertex buffers), which are also transferred and to which the drawing commands refer. In useful embodiments, the stream of drawing commands is separated into individual "command lists" each having a time stamp and relating to one frame, wherein one frame after the other is to be displayed in the drawable region (for an example, see FIG. 4).

The viewing application interprets the drawing commands to generate a time series of frames displayed in the drawable region. By "time series of frames", it is not necessarily meant that the medical image data contains a time series of images (although this is a useful application). The "time series" may also refer to the changes occurring in the drawable region in the usual course of a review session, e.g. the user selects different images for display, makes annotations etc. which can be done in static or moving images, but which causes changes in the diagnostic region (drawable region). The word "frame" is used here to describe whatever is displayed within the drawable region at one time point.

In useful applications of the invention, the viewing application has a, preferably very simple, interpreter that will interpret the stream of drawing commands and generate drawing calls, e.g. for the browser's graphics API (in case of a web application). This can e.g. be WebGL or any other graphics library, like e.g. PaperJS or EaslJS. In useful applications, a high-performance hardware-accelerated graphics API is used, like WebGL. The helper(s) and the viewing application are connected in such a way that they know each other's state. Since the viewing application is able to cache drawing commands, sequences of drawing commands and associated data buffers, e.g. textures, images, vertices or vertex buffers, the helper will not transfer cached drawing commands again and/or will transfer a drawing command relating to only a difference between one frame and the next. This drastically reduces the amount of data to be transferred, since very often the display in the drawable or diagnostic region will change only gradually. For example, if by user interaction an annotation is changed or a line is drawn in, the underlying image (or texture) will not be resent by the helper, but only the drawing commands relating to the exchanged items such the annotations, lines or other overlays. Thus, when only one item in the drawable region has changed, the helper may transfer an update drawing command, which includes instructions on this changed item, and otherwise tells the viewing application to re-execute the drawing calls for the last frame.

In the case of dynamic images (i.e. animated or moving), for example a time series of 2D or 3D images, e.g. acquired from the heart, the helper process will not resend the overlays but only the image content. If a time series of images is to be displayed in a loop, i.e. the same sequence of images again and again, also the images are cached by the viewing application on the user's device. In useful embodiments, the viewing application will cache also the time stamps relating to each drawing command list, so that it can play the loop of dynamic images without interaction with the helper.

In useful embodiments, the viewing application is further able to perform some operations within the drawable region directly, usually in response to user input events at the user interface. These input events are not transferred to the helper. In useful applications, these operations relate to display options selected from the group comprising brightness, contrast, tinting, scaling and adding overlays, or to performing measurements on images displayed in the drawable region.

In most embodiments, the medical study data itself is processed by the helper, which transfers the results of such processing to the viewing application in the form of the stream of drawing commands. The original medical study data, in the format in which it is stored on the platform, is in most embodiments not transferred to the viewing application.

In some embodiments of the invention, the viewing application and the helper will, at the beginning of each session, agree on which functionalities are to be performed by each, based on the bandwidth of the network connection and/or the performance capabilities of the viewing application or the user's device. For example, if the processor on the user's device is slow, whereas the communication channel between viewing application and helper is fast, more data processing functionalities will be performed by the helper, and the results transferred to the viewing application. In an opposite situation, more functionalities might be performed by the viewing application on the user's device.

Since the helper is stateful, which means e.g. that it remembers what was already transferred to a particular viewing application in the course of a review session, useful embodiments of the invention comprise regularly saving the state of the helper, wherein the "state" comprises information e.g. about the active medical study, which measurements were done and the respective results, and which viewport was active, possibly a set of drawing commands necessary to restore the last image rendered in the drawable region. In useful embodiments, the "state" or "state information" is transferred to and stored by the viewing application at regular intervals. Alternatively, it may be stored in the server environment, e.g. by the coordinator engine. Therefore, if a review session is unexpectedly terminated because of a crash either of the helper or the viewing application, it can be continued by a fresh helper, e.g. allocated by the coordinator engine. It may also be useful to store the state of the helper at the end of a review session, so that it may be continued at another time.

The invention is also directed to a method carried out by a server environment, in particular a helper process and possibly a coordinator engine.

The invention is further directed to a computer program product loadable into the internal memory of a digital computer, comprising software code portions for performing the inventive method when said product is run on a computer. It is further directed to a non-transitory computer readable medium comprising a set of instructions that when executed by a processor, result is a series of steps being performed, which carry out the inventive method. The invention may further be implemented in a tangible computer-readable storage medium including computer program code to be executed by a processor, the computer program code, when executed, to implement the inventive method.

BRIEF DESCRIPTION OF THE DRAWINGS

Useful embodiments of the invention are now described in more detail in relation to the attached drawings, in which.

DETAILED DESCRIPTION

Figure 1:
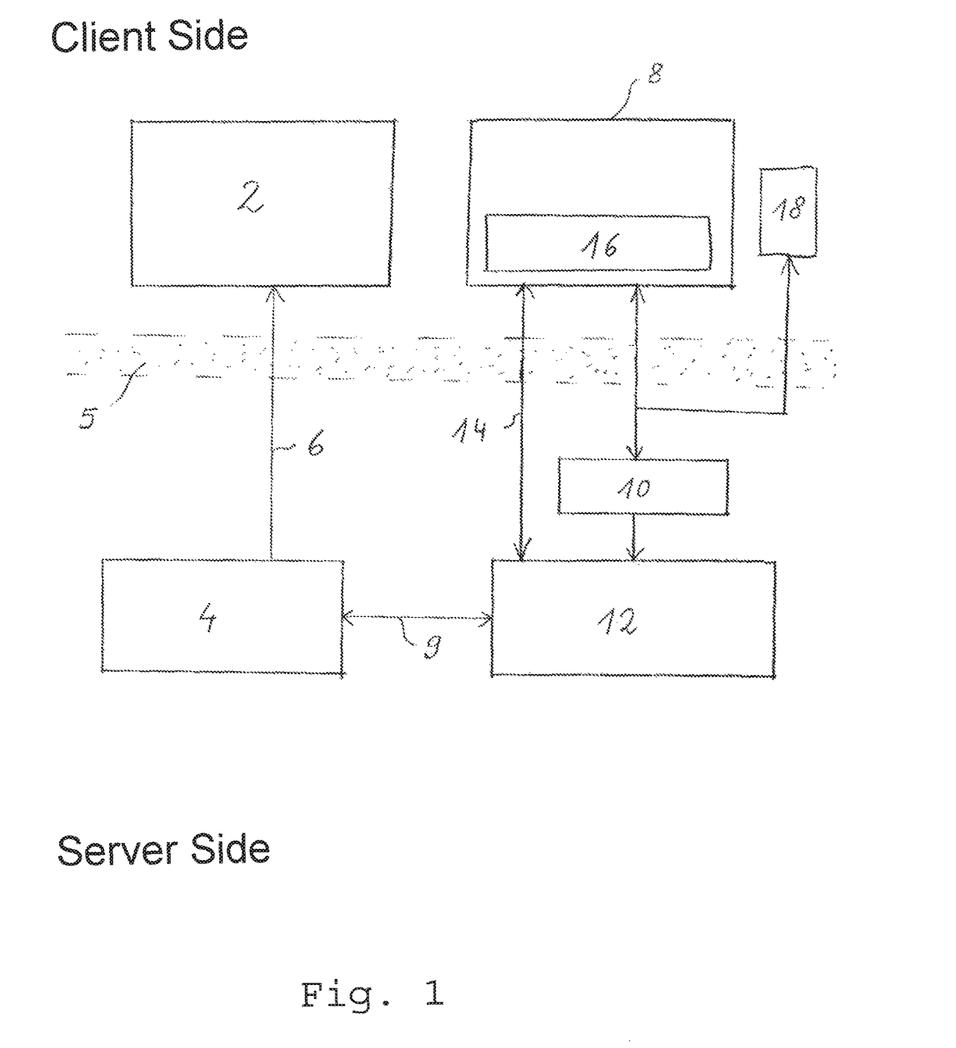
FIG. 1 shows an example of a system overview.

The general system overview on FIG. 1 shows the client side, i.e. the processes running on the user's device, on top, and the server side in the bottom, with a network 5, such as the internet, as intermediate. The server side ("server environment") may consist of multiple machines.

Before starting or at the beginning of a review session, the client or viewing application receives a list of medical studies containing e.g. a list of study identifiers from a platform 4, e.g. a remote server like the PACS of a hospital or other medical institution, and displays it at 2 to the user. The user may select a study, and information (including e.g. the study identifier) on the selected medical study is passed on to the helper process 12. The viewing application 8 will connect to the helper process 12 usually through the intermediation of a coordinator engine 10, which is responsible e.g. for launching, tearing down and migrating helper processes 12. Once the coordinator engine has allocated a helper process 12, at least one communication channel 14 or multiple connections, for example an interactive web socket communication, is established between the stateful helper process 12 and the viewing application 8. The helper 12 can access the platform 4 to retrieve the medical study data after receipt of the study identifier from the viewing application, for example via a HTML connection 9.

In useful embodiments, the viewing application 8 will at the start of a review session send information about its capabilities, for example which texture compression algorithms are supported, to the helper 12, and the helper will accordingly adapt its stream of drawing commands to these capabilities, for example by sending textures in a compressed format optimized for the viewing application 8.

The helper 12 maintains the complete scene graphs and sends drawing commands to the viewing application 8, which allows the viewing application 8 to render the scene graph on the drawable region. Since the helper knows the state of the client (=viewing application) it may send only "delta" updates, i.e. drawing commands relating to the difference between one frame and the next.

The viewing application 8 includes an interpreter 16 which is able to interpret or decode the stream of drawing commands received from the helper 12 and generate drawing calls which are directly executable and executed on the user device, for example by its web browser.

Important states are saved from time to time to a helper state storage 18, which may be on the user's device or alternatively also within the server environment, or on even another server. The stateful helper process 12 is in most applications working per-review session, i.e., it is not re-used but terminated after each review session.

Figure 3:
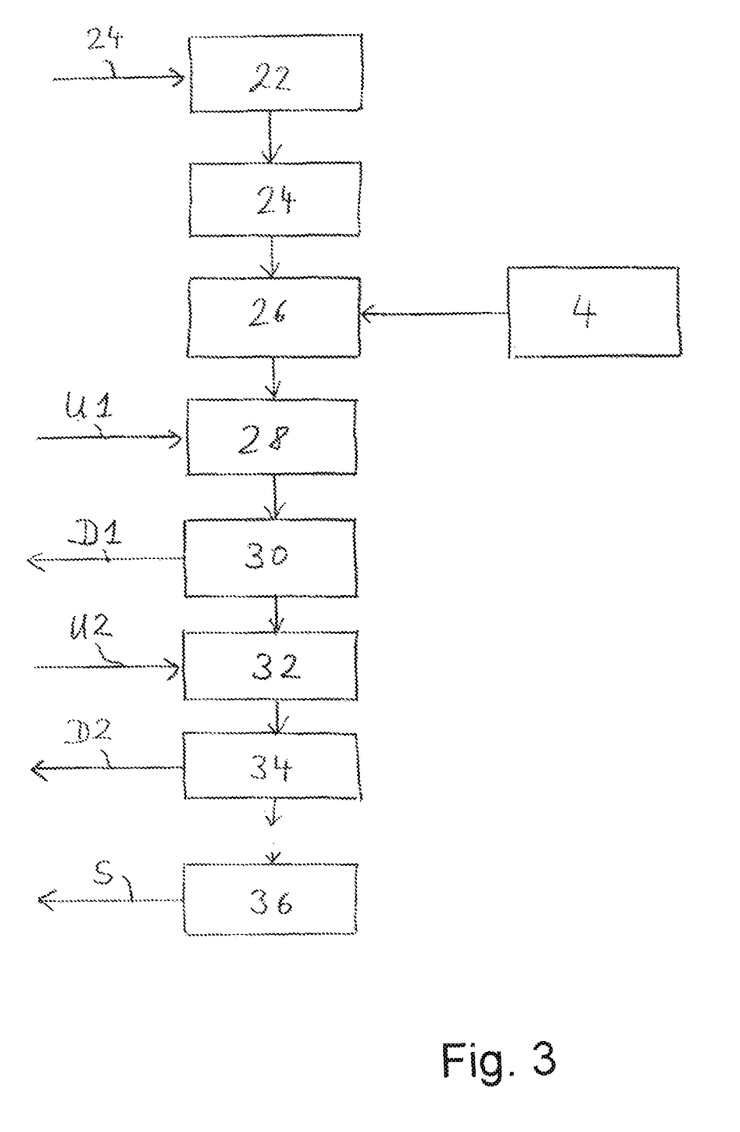
FIG. 3 shows an embodiment of a method performed by a server environment.

FIG. 3 illustrates a method for allowing a user to review medical study data on the user's device, in response to a user sending a request 24 for a review session to a server. In response, one or several helper processes 12 are allocated in step 22 to this review session. At 24, a communication channel is established between the client (viewing application) and the helper, and in many embodiments the viewing application will transfer information about its capabilities, e.g. its available processing capacities, available software components such as texture, compression formats and possibly the bandwidth of the communication channel, to the helper. Information about the bandwidth of the communication channel may be regularly updated during a review session, since the network performance may change during one review session, and the helper can then adapt its stream of drawing commands accordingly (e.g. use stronger compression in a low-bandwidth network).

The helper will also receive information about the active medical study and will retrieve medical study data from the data storage or platform 4 in step 26. In step 28, the helper will optionally receive another user input U1, which may prompt the helper to process the medical study data, for example retrieve certain images and produce textures and possibly overlays therefrom. In step 30, the helper 12 encodes a stream of drawing commands D1, which transfers to the viewing application 8 through the communication channel. These drawing commands D1 are interpreted by the viewing application into suitable drawing calls which draw a suitable display into the drawable region 42 of the viewing application. The user may perform some interaction in the drawable region 42, for example draw in a line to perform a measurement. This user input U2 is transmitted to the helper process in step 32, and the helper process accordingly generates further drawing commands D2 in step 34 which are transferred to the viewing application. In useful embodiments, such drawing commands D2 are optimized by taking into account the state of the viewing application, in particular what has been cached at the viewing application and therefore does not have to be resend.

When the user wishes to end the review session in step 36, the helper process might send information on its state S to a server or to the client side 18 for storage.

Figure 2:
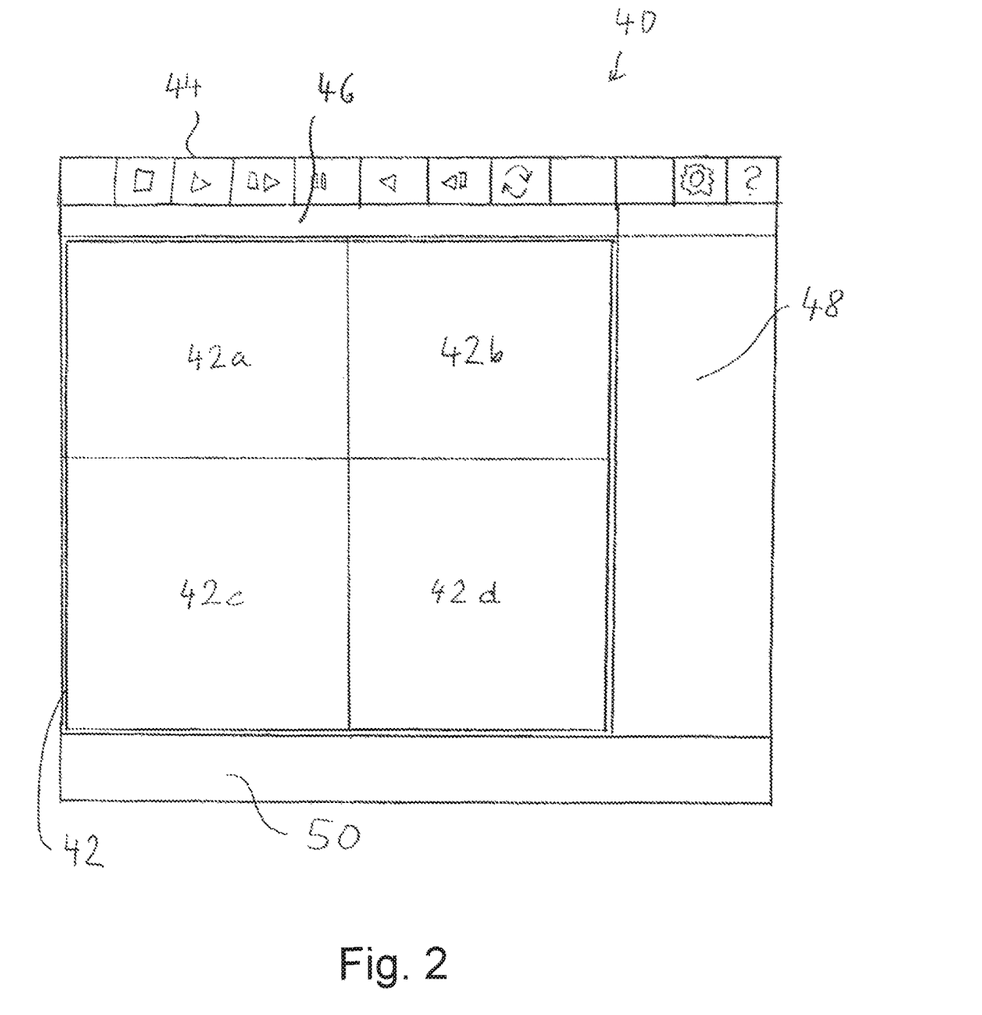
FIG. 2 shows an example of a screenshot of a viewing application running on a user's device.

FIG. 2 shows an example of a client, i.e. a viewing application which may be a web application running inside a user's web browser. The viewing application creates a user interface 40, which includes a drawable region 42. The drawable region 42 may for example be a WebGL canvas. It may be divided into multiple viewports (in this example four) as shown, the viewports being numbered 42a, 42b, 42c and 42d. The drawable region 42 is also called diagnostic region. It is the area on the screen where the drawing calls, which are interpreted by the viewing application 8 from the stream of drawing commands D1, D2, are displayed/rendered. In addition, the user interface includes user input elements such as a tool bar 44 and optionally controls 48. In addition, there may be a status bar 46 and an area for a thumbnail preview 50.

Figure 4:
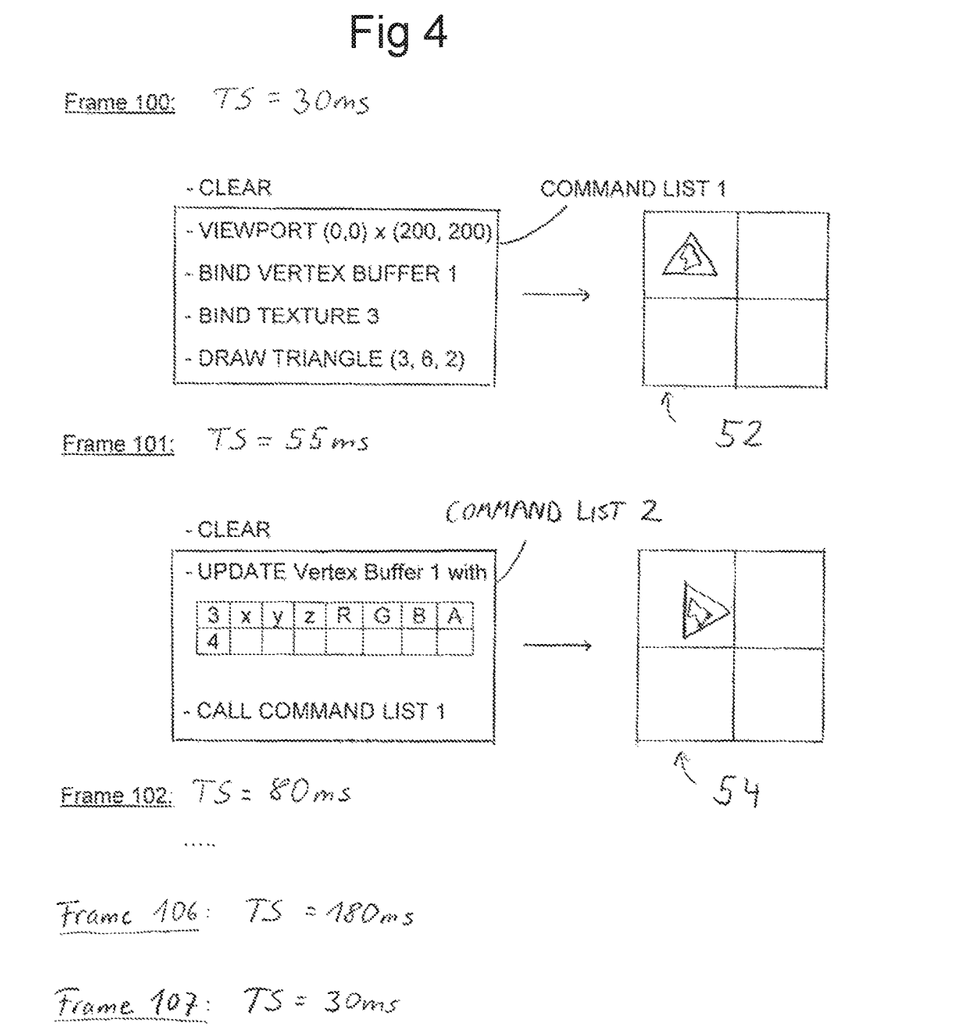
FIG. 4 shows an example of a stream of drawing commands.
Figure 5:
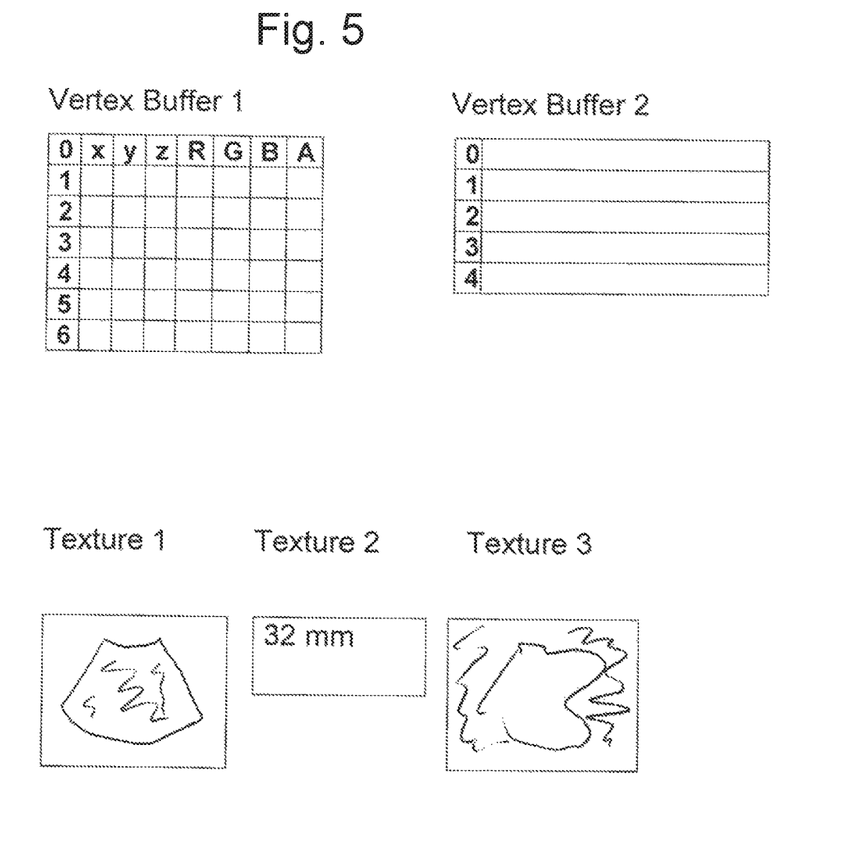
FIG. 5 shows examples of vertex buffers and textures.

The interaction between the helper process and the viewing application, in particular the stream of drawing commands and how they are cached by the viewing application, are illustrated by the example shown in FIGS. 4 and 5.

Initially, the viewing application does not have any scene information received, but wishes to render a frame 100 with time stamp 30 ms on a given time line. The helper knows about the client's state (i.e. that he does not yet have any scene information) and will initially send the necessary vertex buffers and textures, as depicted in FIG. 5. In this example, there are two vertex buffers and three textures. A texture in this context may contain image data extracted from the medical study data (textures 1 and 3 in FIG. 5) or for example an annotation such as texture 2. A vertex is e.g. a node in a graph. Accordingly, the helper sends command list 1 to the viewing application to enable it to draw frame 100 into the drawable region, to be displayed at time stamp 30 ms. After clearing the screen, the drawing command "viewport (0,0)×(200, 200)" indicates that the upper left window is to be used, which reaches from coordinate 0,0 to 200, 200. The viewing application is then instructed to use vertex buffer 1 and texture 3 and to draw a triangle using vertices 3, 6 and 2. These drawing commands are interpreted and executed by the viewing application, and the result is shown at 52.

In a following frame 101 at time stamp 55 ms, the triangle should be slightly changed, so that vertices 3 and 4 are moved. Since everything else remains the same, and the helper knows that the viewing application has all information to draw frame 100, it will now only send an update command to replace vertex number 3 and 4 in vertex buffer 1 and re-issue the drawing sequence. This is shown in command list 2, where vertex buffer 1 is accordingly updated. Then, the drawing command is to call command list 1, accordingly the same drawing commands are executed with an updated vertex buffer 1 (or, in other words, a exchanged vertices number 3 and 4). The result is shown at 54. With this difference-encoding scheme, only the data that has been changed is transferred over the communication channel, resulting in a very low amount of data transferred over the network.

In order to further reduce the amount of data that is transferred, useful embodiments of the invention employ data compression or data deduplication algorithms. This can be done very effectively, because the helper can adapt itself to the viewing application: Different user's devices may use different techniques, for example for texture compression, in particular different mobile devices. Therefore, an optional feature of the invention is that the viewing application will at the beginning of the review session send information about the techniques and in particular which texture compression algorithms it supports, and accordingly the helper will adapt the stream of drawing commands to the viewing application's capabilities. For example, the helper may send the textures in a format optimized for the client (viewing application). Alternatively, the helper may compress textures in JPEG or PNG and the viewing application will decompress them. The viewing application can cache the textures and for example load them onto a graphics card (e.g. via web GL). WebGL texture compression is useful since this is different to other systems: The helper knows which texture compression the client/viewing application needs and sends the textures ready to be downloaded onto the graphics card. This way the client code can cache the compressed texture and uncompression is "for free" on the graphics card.

In addition, helper and viewing application may adapt to the network bandwidth. For example, in slow communication channels, the resolution of the textures may be reduced, or the compression may be raised. Since the helper transfers only drawing commands (and not rendered images), the overlays (such as text annotations, measurements, ECGs etc.) may still be depicted sharply, and only the textures (the image data) is displayed in reduced quality.

Accordingly, the amount of data that is transferred from helper to viewing application may be further reduced e.g. with compression on the network protocol and sophisticated delta compression algorithms like z-delta or other deduplication algorithms.

Figure 6:
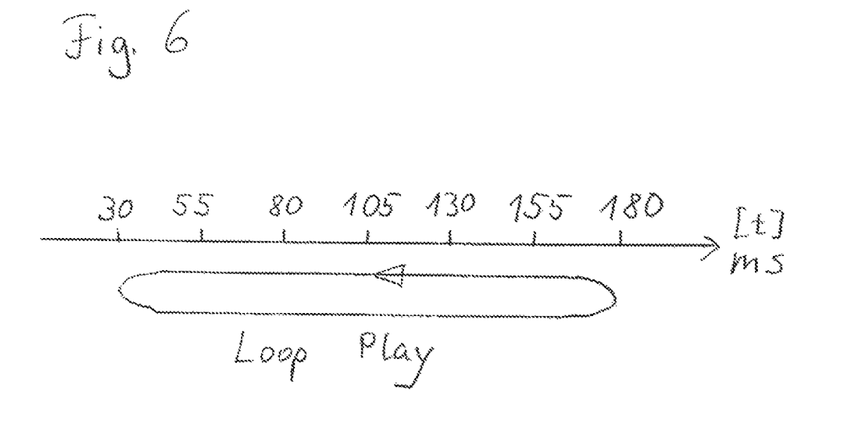
FIG. 6 shows an illustration of animated image data when reviewed by the inventive method.

A further example is the review of animated frames, i.e. a time series of medical images. An example is cardiac imaging, where for example 5-50 images are acquired from the heart during one heart cycle and which have to be displayed in a loop at real-life speed, as illustrated in FIG. 6. Many prior art web-based medical image viewers fail when it comes to animated frames with high frame rates. This is e.g. needed for accurate, diagnostic review of ultrasound examinations. Here both image quality and playback speed must be precise.

This problem can be solved by the invention, as explained by way of an example in the following: Given a medical dataset where we have images at equally distributed timestamps of 25 ms (equals 40 frames per second), we would like to play a loop from timestamp 30 ms to timestamp 180 ms, as depicted in FIG. 6. FIG. 4 lists some of the timeframes (Frame 100 to 106), and we shall assume that we do not change the triangle's coordinates but rather change the triangle's texture image in each frame. So for Frame 101 we would have an update texture call that would replace the texture image with a new image.

Rather than overwriting the texture image, the viewing application now also caches data over time, so it stores the texture images and the delta for the drawing commands to go from Frame 100 to 101, 101 to 102, . . . , and 105 to 106. For Frame 106, which is the last frame in the loop, we then need to go to the first frame again. Since the viewing application only stores the difference or "delta" it cannot draw a frame "out of the sequence", so instead we generate the delta to go from timestamp 180 ms back to timestamp 30 ms, which is our new Frame 107. When this sequence has finished, the viewing application has all information to play the entire loop without any data transferred from the helper. Adding more drawing primitives (like drawing a line or placing a text label) will trigger an update of only a small part of the drawing sequence and we will soon be back to the level where the viewing application can play the loop on its own.

In many embodiments, there is a one-to-one relation between helper and viewing application, but there are embodiments with multiple viewing applications, e.g. mirror applications (tele consulting, recording, multi-monitor broadcast), and/or with multiple helpers (e.g. multiple examinations, different helpers for clinical tasks). In advantageous embodiments, the cache architecture on the client side (viewing application) may comprise capabilities for caching textures (key and frame, or e.g. MD5 hash), caching drawing commands (e.g. frame draw calls) and/or caching vertices, e.g. in vertex buffers. In some embodiments, WebGL (graphics card texture memory) is used as the viewing application's cache In useful embodiments, the helper state data is stored by the viewing application (e.g. browser) on the user's device: Instead of using a database or cache on the helper side (server environment), the helper may transfer state information to the client (viewing application) and store it there, possibly also optimized with compression and delta encoding. This way the requirements for the helper environment are low (no database etc.) and the client (viewing application) can re-create its helper via the coordinator engine when e.g. one server machine crashes or can no longer be reached. Since the stored helper state data is only relevant for the helper (the viewing application does not work on this data), it can be encoded and stored in a compact/compressed format. For untrusted environments, this stored data can be encrypted (e.g. with AES), where encryption keys (private/public) remain in the server environment (are not sent to the viewing application). Thus, the user cannot decrypt the data, the user's device only stores the helper state data for later use by another helper.

In useful embodiments, the same program code for a viewing application as a web application can be used in a normal desktop application (thick client) by using an embedded browser such as chromium. This reduces the development costs since only one code path has to be maintained.

The invention claimed is:

1. A method for reviewing medical study data using a viewing application running on a user's device, the method comprising:
creating, with the viewing application, a user interface including a drawable region on the user's device;
sending a request for a review session to a first server;
allocating at least one helper to the viewing application, wherein a helper is a software application on the first or another server,
establishing at least one communication channel between the viewing application and the helper;
retrieving, with the helper, in response to requests from the viewing application, medical study data from a data storag;
processing, with the helper, the medical study data;
generating, utilizing at least part of said retrieved and processed medical study data, a stream of drawing commands;
transferring the stream of drawing commands to the viewing application through the communication channel, wherein the stream of drawing commands encodes medical image data and overlays;
interpreting, with the viewing application, the drawing commands;
rendering, with the viewing application, a time series of frames;
displaying the time series of frames in the drawable region, wherein the overlays are displayed at a resolution different from a resolution of the medical image data, wherein the frames to be displayed in the drawable region on the user's device are not rendered by the helper;
wherein only textures of the medical image data is displayed in lower resolution than the resolution of the overlays; wherein the stream of drawing commands is separated into individual drawing command lists, each drawing command list having a time stamp and relating to one frame of the time series of frames;
wherein at least part of the drawing command lists are cached on the user's device, so that the helper will not transfer the cached drawing command lists again and will transfer a drawing command list relating only to a difference between one frame and the next,
wherein the medical study data includes a time series of medical images, which are displayed in the time series of frames in the drawable region in a loop, and
wherein the viewing application caches drawing command lists including data buffers containing image data to be displayed, the cached drawing command lists relating only to a difference between a final medical image within the time series and a first medical image within the time series, as well as time stamps relating to each medical image within the time series, so that it is able to display the loop without intervention of the helper.

2. A method according to claim 1, wherein the viewing application is a web application running inside an internet browser, a desktop application, or a mobile application.

3. A method according to claim 1, wherein the viewing application is loaded onto the user's device from a web-server without user interaction, preferably before each review session.

4. A method according to claim 1, wherein the viewing application includes an interpreter engine as software part running on the user's device and which is capable of interpreting the drawing commands received from the helper and translating them into drawing calls which are readable by software or hardware already present on the user's device.

5. A method according to claim 1, wherein the viewing application is capable of performing some operations within the drawable region without receiving drawing commands from the helper, wherein these operations preferably relate either to display options selected from the group comprising brightness, contrast, tinting, adding overlays, and scaling, or to performing measurements on images displayed in the drawable region.

6. A method according to claim 1, wherein the helper is allocated by a coordinator engine as software part running on the first or other server, wherein the coordinator engine is configured to allocate and optionally start helpers, to balance the load within the server environment in which the helpers are running, or to ensure initial authentication of the user.

7. A method according to claim 1, wherein the helper is configured to receive user input information from the viewing application, to process said user input, in particular by making measurements on the medical study data or editing the medical study data, and to transfer the results of such processing to the viewing application as part of the stream of drawing commands.

8. A method according claim 1, wherein the stream of drawing commands includes associated data buffers and the overlays include text annotations and graphical displays.

9. A method according to claim 1, wherein if only part of the items to be rendered in the drawable region changes from one frame to the next, the helper will transfer an update drawing command for each new frame, in particular a command to exchange the changed item or items and to re-execute the drawing calls for the last frame with the exchanged items.

10. A method according to claim 1, wherein a state of the helper is transferred to and stored by the viewing application at regular intervals, in particular at the end of a review session.

11. A method for allowing a user to review medial study data on a user's device in response to the user sending a request for a review session from a viewing application running on the user's device to a first server, the method comprising the following steps:
  allocating, in response to the user's request for the review session, at least one helper process running on the first or another server to the viewing application;
  passing communication information to the viewing application;
  establishing at least one communication channel between the viewing application and the helper viewing application to establish at least one communication channel between the viewing application and the helper;
  retrieving, with the helper, medical study data from a data storage;
  processing, with the helper, the medical study data;
  encoding, with the helper, utilizing at least part of said retrieved or processed medical study data, a stream of drawing commands;
  transfering, with the helper, the stream of drawing commands to the viewing application through the at least one communication channel, wherein the stream of drawing commands encodes medical image data and overlays, rendering frames for display, based on the stream of drawing commands, wherein the frames to be displayed in a drawable region on the user's device are not rendered by the helper;
  adapting the stream o drawing commands, wherein the helper knows a state of the viewing application and the helper does not reseed at least some drawing commands which have been cached by the viewing application;
  displaying a time series of medical images included in the medical study data and the overlays, wherein the time series of medical images and the overlays are displayed in the time series of frames in the drawable region in a loop, wherein the overlays are displayed at a resolution different from a resolution of the medical image data;
  wherein only textures of the medical image data is displayed in lower resolution than the resolution of the overlays, wherein the stream of drawing commands is separated into individual drawing command lists each drawing command list having a time stamp and relating to one frame of the time series of frames; and
  caching, with the viewing application, the drawing command list including data buffers containing image data to he displayed, the drawing command list relating only to a difference between a final medical image within the time series and a first medical image within the time series, as well as time stamps relating to each medical image within the time series, so that the viewing application is able to display the loop without intervention of the helper.

12. A method according to claim 11, wherein the helper is allocated by a coordinator engine on the first or another server, wherein the coordinator engine is configured to allocate and optionally start helpers, to balance the load within a server environment in which the helpers are running, or to ensure initial authentication of the user.

13. A method according to claim 11, wherein the helper is configured to receive user input information from the viewing application, to process said user input, in particular by making measurements on the medical study data or editing the medical study data, and to transfer the results of such processing to the viewing application as part of the stream of drawing commands.

14. A method according claim 11, wherein the stream of drawing commands includes associated data buffers and the overlays include text annotations and graphical displays.

15. A method according to claim 11, wherein if only part of the items to be rendered in the drawable region changes from one frame to the next, the helper will transfer an update drawing command for each new frame, in particular a command to exchange the changed item or items and to re-execute the drawing calls for the last frame with the exchanged items.

16. A method according to claim 11, wherein a state of the helper is transferred to and stored by the viewing application at regular intervals, in particular at the end of a review session.

17. A non-transitory computer readable medium having stored thereon a computer program product comprising software code portions for performing the method of claim 1 when said product is run on a computer or on several computers connected via a network such as the internet.

18. A computer system comprising:
  a viewing application running on a user's device configured to create a user interface including a drawable region on the user's device;
  a server environment including
    a coordinator engine to receive requests for review sessions from the viewing application, and
    at least one stateful review helper process,
  wherein one helper process is allocated to each review session by the coordinator engine, the helper process retrieves medical study data from a data storage and transfers a stream of drawing commands to the viewing application, wherein the stream of drawing commands encodes medical data including medical image data, as well as overlays, including text annotations and graphical displays,
  wherein the medical study data includes a time series of medical images, which are displayed in the time series of frames in the drawable region in a loop, wherein the overlays are displayed at a resolution different from a resolution of the medical image data, wherein only textures of the medical image data is displayed in lower resolution than the resolution of the overlays, wherein the stream of drawing commands is separated into individual drawing command lists each drawing command list having a time stamp and relating to one frame of the time series of frames, and
  wherein the viewing application caches the drawing command lists including data buffers containing image data to be displayed, the drawing command lists relating only to a difference between a final medical image within the time series and a first medical image within the time series, as well as time stamps relating to each medical image within the time series, so that it is able to display the loop without intervention of the helper.

* * * * *